United States Patent [19]

Raymond

[11] 4,296,745

[45] Oct. 27, 1981

[54] SURGICAL SEALANT COMPOSITION

[75] Inventor: Christopher D. Raymond, High Wycombe, England

[73] Assignee: G. D. Searle & Co., Skokie, Ill.

[21] Appl. No.: 93,351

[22] Filed: Nov. 13, 1979

[30] Foreign Application Priority Data

Nov. 20, 1978 [GB] United Kingdom ............... 45281/78

[51] Int. Cl.$^3$ ............................................ A61L 15/00
[52] U.S. Cl. .................................... 128/156; 128/283; 428/262; 260/31.8 N
[58] Field of Search .............................. 128/155–156, 128/283; 428/262; 260/29.1 R, 31.8 N

[56] References Cited

U.S. PATENT DOCUMENTS

| | | | |
|---|---|---|---|
| 2,451,865 | 10/1948 | O'Brien | 128/156 |
| 2,728,687 | 12/1955 | Hrerre | 128/156 X |
| 2,734,503 | 2/1956 | Doyle | 128/156 |
| 3,103,858 | 9/1963 | Lauren | 128/156 X |
| 3,980,084 | 9/1976 | Kross | 128/283 |
| 4,147,831 | 4/1979 | Balinth | 128/156 |
| 4,153,055 | 5/1979 | Etes | 128/283 |
| 4,192,785 | 3/1980 | Chen et al. | 128/283 |
| 4,213,458 | 7/1980 | Nolan et al. | 128/283 |
| 4,222,923 | 9/1980 | Rhodes et al. | 128/283 |

FOREIGN PATENT DOCUMENTS 1088992 10/1967 United Kingdom .
1131397 10/1968 United Kingdom .

Primary Examiner—C. Fred Rosenbaum
Attorney, Agent, or Firm—Albert Tockman; Daniel J. Long

[57] ABSTRACT

An adhesive surgical dressing which comprises a backing material provided on one side with a composition comprising per 100 parts, by weight, of a non-biodegradable, tacky, polymeric binding agent, from 12 to 25 parts, by weight, of an inert reinforcing filler and a coating on at least the intended skin contacting face of the dressing of a non-biodegradable, water-activated adhesive/thickner, the composition having an aqueous swell value of from 5 to 40% and a cold flow value of from 50 to 90%, is disclosed.

An adhesive surgical dressing composition which comprises per 100 parts, by weight, of a non-biodegradable, tacky, polymeric binding agent, from 5 to 150 parts, by weight, of a non-biodegradable, water-activated adhesive/thickner and from 12 to 25 parts, by weight, of an inert reinforcing filler, is also disclosed.

The adhesive material obviates certain disadvantages of known materials in that it adheres satisfactorily to moist surfaces, it absorbs moisture and maintains its adhesion and is physiologically acceptable.

10 Claims, No Drawings

SURGICAL SEALANT COMPOSITION

This invention relates to a surgical sealant composition; more particularly, it relates to such a composition for use in the preparation of adhesive surgical dressings, for example sealing rings for post surgical drainage pouches and surgical dressings in strip form.

Following certain surgical procedures, such as colostomy and ileostomy, there is provided in the abdominal wall a permanent opening, the stoma, through which drains the contents of that portion of the intestine which has been surgically modified. The material draining through the opening is collected in a pouch sealed to the skin surface surrounding the opening. Conventionally, such pouches are sealed to the skin by an adhesive sealing ring which surrounds the stoma and seals the pouch to the skin. In other cases, where the stoma aperture is irregular in shape, strips of adhesive material may be used to build up a suitable seal.

The necessary properties for the material of the sealing ring or strip are demanding. The area of the skin to which the ring is to adhere is moist, liable to discharge, subject to flexure and very susceptible to infection and irritation. Thus, the adhesive material needs to adhere satisfactorily to a moist surface, be capable of absorbing moisture and maintaining its adhesion and its needs to be physiologically acceptable in that it should not produce irritation to the sensitive area with which it is in contact. Some of the conventionally available stoma sealing rings show certain disadvantages in use, namely they swell to an unacceptable degree in the presence of moisture resulting in a reduction in mechanical properties; in some cases, the cold flow of the composition is too high and this results in loss of shape; furthermore, many of the compositions contain bio-degradable components, as a result of which the composition becomes weakened in use.

It has now been found that these disadvantages may be obviated or substantially reduced by forming a stoma sealing ring or strip-form surgical dressing from a composition comprising a non-biodegradable, tacky, polymeric binding agent, having at least the skin contact surface provided with a coating of a water-activated, non-biodegradable adhesive/thickner, the composition being filled with an inert reinforcing filler.

Accordingly, in one embodiment of the present invention, there is provided an adhesive surgical dressing, particularly a stoma sealing ring, which comprises a backing material provided on one side with a coating of a composition comprising per 100 parts, by weight, of a non-biodegradable, tacky, polymeric binding agent, from 12 to 25 parts, by weight, of an inert reinforcing filler and a coating on at least the intended skin contacting face of the dressing of a non-biodegradable, water-activated adhesive/thickner, the composition having an aqueous swell value of from 5 to 40% and a cold flow value of from 50 to 90%.

In another embodiment of the present invention, the non-biodegradable water-activated adhesive/thickner is generally dispersed throughout the composition and in this aspect the present invention provides an adhesive surgical dressing composition generally for use in the preparation of surgical dressings, more particularly stoma sealing rings, which comprises per 100 parts, by weight, of a non-biodegradable tacky, polymeric binding agent, from 5 to 150 parts, by weight, of a nonbiodegradable water-activated adhesive/thickner and from 12 to 25 parts, by weight, of an inert reinforcing filler.

All compositions according to the present invention show acceptable values for cold flow and swell, namely a degree of swelling of from 5 to 40% and a degree of cold flow of from 50 to 90%. Preferred values are: swelling $10\pm5\%$; cold flow $65\pm5\%$.

Degree of swelling is measured as the percentage increase of 1 cm$^2$ of the composition in deionised water at ambient temperature over 60 minutes. Cold flow is measured as the retention of thickness of a sample of the composition under a compressive weight of 4.5 kg.

Examples of suitable polymeric binding agents include: polyisoprene, polyurethane, silicone and polyisobutylene. The preferred class of binding agents are polyisobutylenes having a molecular weight (Stanudinger) of from 8000 to 15000. A particularly preferred binding agent is the polyisobutylene having a molecular weight of from 8700 to 10000 sold under the trade name "Vistanex LM/MS" by Esso Chemicals.

Polyacrylamides having a molecular weight of from $1\times10^6$ to $6\times10^6$ and a particle size of from 100 to 1000 microns have been found to be suitable adhesive/thickners. A preferred polyacrylamide is that sold by Cyanamid BV, Netherlands, under the trade name "Cyanamer P250" which has a molecular weight of from $5\times10^6$ to $6\times10^6$ and a particle size expressed as 12% retained on a 780 micron sieve and 30% passing through a 150 micron sieve.

Bearing in mind aesthetic considerations, any of the conventional reinforcing fillers may be used in the present composition. Preferred reinforcing fillers are precipitated or fume silicas having a B.E.T. surface area (m$^2$/g) of from 175 to 420 and an average particle size of from 7 to 15 microns. A particularly suitable material is the fume silica 'Aerosil 200v' sold by Degussa of Frankfurt am Main, Germany, which has a B.E.T. surface area of $200\pm25$ m$^2$/g and an average particle size of 12 microns.

Generally, for use as a stoma sealing ring the composition is formed in the desired shape and that surface to be in contact with the skin is covered with a release paper to be removed immediately before application and the other face is covered by a protective backing layer, such as a microporous polymer sheet, for example a film of microporous polyethylene. The microporous nature of the polymer sheet allows the passage of water through the sheet as it builds up in the sealing ring composition. In order to ensure satisfactory removal of the release paper the composition may also contain a release promoting agent, such as polyethylene, dispersed throughout the composition or present in the surface of the composition to be in contact with the release paper. The polyethylene should have a molecular weight of from 1500 to 48000, a preferred material is the Allied Chemical polyethylene 617 A which has an average molecular weight of 1500. If included dispersed through the composition, the polyethylene is present in an amount of from 5 to 50 parts, by weight. In some circumstances, it may be desirable to increase the water absorbing capacity of the composition, in which case the composition may also include up to 40 parts, by weight, of a synthetic swelling clay, particularly synthetic hydrous magnesium silicate clay preferably having a particle size of from 100 to 1000 microns, such as "Laponite XLG" produced by Laporte Chemicals Ltd. Where a hydrous magnesium silicate clay is included in the composition, the composition is rendered alkaline to such a degree that may be unacceptable and, therefore, a pH adjuster should be included to bring the pH of the composition to an acceptable value of the order of from 6 to 7. Generally, up to 4 parts, by weight, of pH adjuster is used. The pH adjuster should be such that it is not leached out of the composition by the moisture. Certain carboxy-polymethylene polymers, e.g. those having a molecular weight of from 250,000 to 4,000,000 and a particle size of from 1 to 100 microns, particularly "Carbopol 934" sold by B. F. Goodrich Chemical Co., have proved satisfactory. The quantity of the pH adjusting agent included will be dictated by the amount of and the nature of the hydrous magnesium silicate clay present; from 0.4 to 4 parts of Carbopol 934 has been found to be adequate.

In a preferred embodiment, the present composition, therefore, has the following formulation-

| Component | Parts, by Weight |
|---|---|
| Tacky polymeric binder ("Vistanex LM/MS") | 100 |
| Water-activated adhesive/thickener ("Cyanamer P25P") | 5-150 |
| Synthetic swelling clay ("Laponite XLG") | 0-40 |
| Inert reinforcing filler ("Aerosil 200v") | 12-25 |
| pH adjuster ("Carbopol 934") | 0-4 |
| Release promoter ("AC polyethylene 617A") | 0-50 |

The present composition may be mixed in a conventional manner using, for example, a Z-blade mixer developing a temperature of the order of 90° C. in the composition. The reinforcing filler should be added to the mix as the last component. The composition is then extruded as a blank and rolled at 90° C. to the desired thickness, e.g. 1.6 mm, between silicone release paper on the one face and the polyethylene protective film on the other face.

Although the present composition has been described as being particularly useful for creating a backing material to form an adhesive dressing, particularly a stoma sealing ring, the composition also has utility in the area of stoma care as a packing, to be used without a backing material. This use is relevant for the packing of the area surrounding a stoma where the stoma is not of a regular shape or where the skin surrounding the stoma is puckered.

Accordingly, as mentioned above, the present invention also provides a surgical dressing composition comprising per 100 parts, by weight, of a non-biodegradable tacky, polymeric binding agent, from 5 to 150 parts, by weight, of a non-biodegradable water-activated adhesive/thickner and from 12 to 25 parts, by weight, of an inert reinforcing filler.

This composition may also contain the synthetic hydrous magnesium silicate clay and the pH adjuster referred to above. Although the polyethylene component referred to above functions at least in part as an aid to the removal of the release paper used to cover the stoma sealing ring it may also be included in the composition to be used without backing material since it acts also as a processing aid in making up the composition.

The following Examples illustrate the present invention (the compositions are suitable for use in the production of stoma sealing rings):

EXAMPLE 1

| Component | Parts, by Weight |
|---|---|
| "Vistanex LM/MS" | 100 |
| "Cyanamer P250" | 60.0 |
| "Laponite XLG" | 20.00 |
| "Aerosil 200v" | 18.0 |
| "Carbopol 934" | 2.0 |
| "AC polyethylene 617A" | 20.0 |

This composition had the following properties:
Swelling 10%
Cold Flow 58%

EXAMPLE 2

| Component | Parts, by Weight |
|---|---|
| "Vistanex LM/MS" | 100 |
| "Cyanamer P250" | 70.0 |
| "Aerosil 200v" | 20.0 |

This composition had the following properties:
Swelling 14%
Cold Flow 73%

EXAMPLE 3

| Component | Parts, by Weight |
|---|---|
| "Vistanex LM/MS" | 100 |
| "Cyanamer P250" | 35.0 |
| "Laponite XLG" | 35.0 |
| "Carbopol 934" | 3.0 |
| "Aerosil 200v" | 18.0 |

This composition had the following properties:
Swelling 37%
Cold Flow 71%

EXAMPLE 4

| Component | Parts, by Weight |
|---|---|
| "Vistanex LM/MS" | 100 |
| "Cyanamer P250" | 60.0 |
| "Laponite XLG" | 10.0 |
| "Carbopol 934" | 2.0 |
| "Aerosil 200v" | 18.0 |
| "AC polyethylene 617A" | 20.0 |

This composition had the following properties:
Swelling 11%
Cold Flow 87%

EXAMPLE 5

| Component | Parts, by Weight |
|---|---|
| "Vistanex LM/MS" | 100 |
| "Cyanamer P250" | 90.0 |
| "Laponite XLG" | 20.0 |
| "Carbopol 934" | 2.0 |
| "Aerosil 200v" | 18.0 |
| "AC polyethylene 617A" | 20.0 |

This composition had the following properties:
Swelling 8%
Cold Flow 64%

I claim:

1. An adhesive surgical dressing which comprises a backing material provided on one side with a composition comprising per 100 parts, by weight, of a non-biodegradable, tacky, polymeric binding agent, selected from a group consisting of polyisoprene, polyurethane, silicone, and polyisobutylene, from 12 to 25 parts, by weight, of an inert reinforcing filler and a coating on at least the intended skin contacting face of the dressing of a non-biogradeable, water-activated polyacrylamide adhesive/thickner.

2. An adhesive surgical dressing as claimed in claim 1 wherein the non-biodegradable, water-activated adhesive/thickner is dispersed throughout the composition and is present in an amount of from 5 to 150 parts, by weight.

3. An adhesive surgical dressing as claimed in claim 1 or claim 2 wherein the reinforcing filler is a fume silica.

4. An adhesive surgical dressing as claimed in claim 1 or claim 2 wherein the backing material is a microporous polymer sheet.

5. An adhesive surgical dressing as claimed in claim 1 or claim 2 wherein the composition also contains up to 40 parts, by weight, of a synthetic swelling clay and up to 4 parts, by weight, of a pH adjuster to produce a pH value for the composition of from 6 to 7.

6. An adhesive surgical dressing as claimed in claim 1 or claim 2 wherein the dressing has, on the intended skin contact face, a removable cover layer and the composition also comprises a release promoting agent in an amount of from 5 to 50 parts, by weight.

7. An adhesive surgical dressing as claimed in claim 1 or claim 2 which is in the form of a stoma sealing ring.

8. An adhesive surgical dressing composition which comprises per 100 parts, by weight, of a non-biogradable, tacky, polymeric binding agent, selected from a group consisting of polyisoprene, polyurethane, silicone, and polyisobutylene, from 5 to 150 parts, by weight, of a non-biogradeable, water-activated polyacrylamide adhesive/thickner and from 12 to 25 parts, by weight, of an inert reinforcing filler.

9. An adhesive surgical dressing composition as claimed in claim 8 also containing up to 40 parts, by weight, of a synthetic swelling clay and up to 4 parts, by weight, of a pH adjuster to produce a pH value for the composition of from 6 to 7.

10. An adhesive surgical dressing composition as claimed in claim 8 or claim 9 having, on the intended skin contact face, a removable cover layer and the composition also comprises a release promoting agent in an amount of from 5 to 50 parts, by weight.

* * * * *